United States Patent [19]

Dunn et al.

[11] Patent Number: 5,324,519
[45] Date of Patent: Jun. 28, 1994

[54] BIODEGRADABLE POLYMER COMPOSITION

[75] Inventors: Richard L. Dunn; Arthur J. Tipton; George L. Southard; Jack A. Rogers, all of Fort Collins, Colo.

[73] Assignee: Atrix Laboratories, Inc., Fort Collins, Colo.

[21] Appl. No.: 783,512

[22] Filed: Oct. 28, 1991

Related U.S. Application Data

[63] Continuation-in-part of Ser. No. 384,416, Jul. 24, 1989, Pat. No. 5,077,049.

[51] Int. Cl.$^5$ .................................. A61F 2/00
[52] U.S. Cl. ........................... 424/426; 424/422; 424/423; 424/424; 424/425; 424/486
[58] Field of Search ............... 424/426, 422, 423, 424, 424/425, 486; 433/201.1; 525/415

[56] References Cited

U.S. PATENT DOCUMENTS

| | | | |
|---|---|---|---|
| 3,068,188 | 12/1962 | Beste et al. | 524/104 |
| 3,919,773 | 11/1975 | Freeman | 433/201.1 |
| 3,949,073 | 4/1976 | Daniels et al. | 514/801 |
| 3,975,350 | 8/1976 | Hudgin et al. | 524/108 |
| 4,294,753 | 10/1981 | Urist | 424/549 |
| 4,451,452 | 5/1984 | Deibig et al. | 424/493 |
| 4,455,256 | 6/1984 | Urist | 530/350 |
| 4,526,909 | 7/1985 | Urist | 530/350 |
| 4,526,938 | 7/1985 | Churchill et al. | 525/415 |
| 4,563,489 | 1/1986 | Urist | 514/21 |
| 4,596,574 | 6/1986 | Urist | 623/16 |
| 4,619,989 | 10/1986 | Urist | 530/417 |
| 4,761,471 | 8/1988 | Urist | 530/350 |
| 4,789,732 | 12/1988 | Urist | 530/350 |
| 4,795,804 | 1/1989 | Urist | 530/350 |
| 4,857,456 | 8/1989 | Urist | 435/7.92 |
| 4,894,373 | 1/1990 | Urist | 514/239.2 |
| 4,902,296 | 2/1990 | Bolander et al. | 623/16 |
| 4,904,478 | 2/1990 | Walsdorf et al. | 424/468 |
| 4,905,680 | 3/1990 | Tunc | 606/69 |
| 4,911,931 | 3/1990 | Baylink | 424/606 |
| 4,916,241 | 4/1990 | Hayward et al. | 549/313 |
| 4,921,697 | 5/1990 | Peterlik et al. | 424/85.5 |
| 4,932,973 | 6/1990 | Gendler | 623/16 |
| 4,938,763 | 7/1990 | Dunn et al. | 604/891.1 |
| 4,939,131 | 7/1990 | Benedict et al. | 514/102 |
| 4,942,157 | 7/1990 | Gall et al. | 514/108 |
| 4,946,870 | 8/1990 | Partain, III et al. | 514/777 |
| 4,961,707 | 10/1990 | Magnusson et al. | 424/424 |

FOREIGN PATENT DOCUMENTS 2223027 8/1989 United Kingdom .

OTHER PUBLICATIONS

K. Juni et al., *Control of Release Rate of Bleomycin from Polyactic Acid Microspheres by Additives*, Chem. Pharm. Bull., 33(4), 1609–1614 (1985).

*Primary Examiner*—Thurman K. Page
*Assistant Examiner*—James M. Spear
*Attorney, Agent, or Firm*—Merchant, Gould, Smith, Edell, Welter & Schmidt

[57] ABSTRACT

The invention is directed to a composition composed of a thermoplastic or thermosetting polymer which is capable of forming a biodegradable and/or bioerodible microporous, solid or gelatinous polymer matrix. The matrix is useful as an implant in animals for enhancing regeneration of cells and tissue, such as bone and nerve cells, or for delivery of biologically-active substances to tissue or organs. The composition is administered to an implant site as a liquid. The invention also includes a method of preventing and treating disorders and diseases, such as bone or nerve growth disorders, or of altering body functions such as birth control, using the compositions and implants of the invention.

26 Claims, No Drawings

BIODEGRADABLE POLYMER COMPOSITION

CROSS-REFERENCE TO RELATED APPLICATIONS

This patent application is a continuation-in-part of U.S. patent application Ser. No. 384,416, filed Jul. 24, 1989, now U.S. Pat. No. 5,077,049.

BACKGROUND OF THE INVENTION

Polymeric implants are useful as delivery systems and/or as mechanical barriers. Implants such as preformed membranes or films have been described. However, many of these implants have limited properties and produce inferior results either as mechanical barriers or delivery systems.

Several implant techniques have been used in medical and dental applications. One application of interest is the use of implants in treatment of periodontal disease. Surgery alone does not result in restoration of lost periodontium. Successful periodontal restoration is known to occur if periodontal ligament cells are allowed to colonize root surfaces preferentially over gingival epithelial cells, gingival fibroblasts or osteoblasts. Microporous membranes, such as the Millipore ® filter and GORE-TEX ® membranes, have been used for periodontal tissue regeneration. Typically, the periodontal flap is cut, and the membrane is surgically inserted to cover the surface of the tooth root and to physically occlude epithelial cells from apically migrating along the root surface.

Those membranes, however, have several drawbacks. Besides variable results, a second surgical entry is needed to remove the membrane after tissue regeneration has been achieved because the membranes are not biodegradable. There is also a higher incidence of infection in connection with their use.

To preclude surgical removal of the implant, membranes made of bioabsorbable material, such as microfibrillar collagen, polylactic acid, and polygalactin (Vicryl ®) mesh have been used. Results have been variable, and the therapeutic effect of these membranes has been unpredictable. In addition, fitting and positioning these membranes to the implant site is time-consuming and cumbersome. The degradation time of membranes composed of collagen has been variable, and the risk of adverse immunological reaction to this foreign protein material in the body presents a major concern.

Therefore, an object of the invention is to provide a composition comprising a biodegradable or bioerodible polymer for use as an implant in an animal including a human. Another object is the development of an implant that will eliminate the need for its surgical removal after its purpose has been achieved. Another object is to provide a composition which may be administered to an implant site in liquid form and which is capable of solidifying in situ to form an implant. A further object of the invention is to provide a biodegradable implant which may be used to enhance connective cell or tissue growth and deter growth of epithelial cells and tissue into the core of the implant. Yet another object is to provide an implant which is capable of delivery of a drug or other medicament over a desired period of time. A further object is to provide an implant for providing controlled release delivery of at least one biologically-active agent for stimulation and/or enhancement of physiological or biological activity in an animal.

SUMMARY OF THE INVENTION

These and other goals are achieved by the present invention which is directed to a composition for providing in situ a biodegradable or bioerodible microporous matrix. The matrix may be used to deliver biologically-active substances and/or for selective enhancement of cell growth and tissue regeneration in animals.

The composition is a liquid formulation of a biocompatible and biodegradable or bioerodible thermoplastic or thermoset polymer or copolymer which is substantially insoluble in aqueous media and body fluids. The composition may include a separate pore-forming agent which is capable of generating additional pores within the polymer matrix. When a biologically-active agent is to be released by the matrix, the agent is dissolved in the composition to form a homogenous solution or dispersed in the composition to form a suspension.

The invention also provides a method of using the composition for preventing and treating diseases and disorders, such as diseases of the bone and connective tissue, infectious diseases, cancer, metabolic disorders and allergies. The invention also provides a method of using the composition for tissue regeneration useful in wound and organ repair, nerve regeneration, periodontium regeneration, and bone regeneration. The invention also provides a method of using the composition for altering the physiological or biological activity of an animal such as reproductive function.

Thermoplastic Polymer Compositions

According to a first embodiment of the invention, the composition is a liquid formulation of a thermoplastic polymer and a pharmaceutically acceptable organic solvent. The composition is administered as a liquid to an implant site, whereupon the solvent diffuses or dissipates into the surrounding aqueous tissue fluids. The thermoplastic polymer is not soluble in these aqueous fluids so that it coagulates or solidifies to form a microporous solid or gelatinous matrix. The matrix preferably has a two-layered pore structure composed of a core portion and an outer surface layer or skin. The polymer matrix is suitable for use as an in situ formed implant in an animal, including humans and other mammals. The composition may be administered to tissue, to a surgical incision, or to a void space in tissue such as a periodontal pocket, and the like.

Thermoset Polymer Compositions

According to a second embodiment of the invention, the composition is a liquid formulation of a thermoset prepolymer or copolymer, preferably an acrylic ester-terminated biodegradable prepolymer, which is capable of cross-linking in situ to form a polymeric or copolymeric solid or gelatinous matrix. The composition preferably is a neat liquid but may include a pharmaceutically acceptable organic solvent that is miscible with water and body fluids.

When the thermoset polymer composition is cross-linked in situ, the resulting matrix is rendered microporous by one of several means. Use of a small but suitable amount of organic solvent will produce pores as described above for the thermoplastic polymer. The prepolymer ingredients may release a pore-forming moiety such as carbon dioxide and the like, or a separate pore-forming agent may be included. The pore-forming agent may be any suitable organic or inorganic substance which is soluble or substantially miscible in water and tissue fluids, and substantially miscible or dispersible in the thermoset polymer composition.

The thermosetting polymer composition may include a curing agent, such as a catalyst, which is capable of enhancing the cross-linking reaction of prepolymers. The curing agent is biocompatible. Preferred catalysts include benzoyl peroxide and azobisisobutyronitrile.

Porosity of the Polymer Matrices

Several factors influence the size, or diameter, of the pores formed in the polymer matrix of the implant. In the polymer matrices formed from the thermoplastic polymer composition and from the thermoset polymer composition containing solvent or pore-forming moiety, the action of the solvent (or pore-forming moiety), as it diffuses out of the coagulating or solidifying polymer matrix and into the surrounding tissue fluids, generates pores in the matrix and produces a two-component structure. The outer component is a surface skin which surrounds the inner component or core. The core contains pores of diameter from about 10 to 1000$\mu$ while the skin is functionally non-porous in comparison with the core. In fact, the skin has pores which are significantly smaller in diameter than those of the core.

The addition of a pore-forming agent to the thermoplastic polymer composition and the use of a pore-forming agent as part of the thermoset polymer composition will produce a matrix having about the same diameter pores throughout the core and skin. The size and/or quantity of a pore-forming agent included in the polymer matrix, and the distribution of the pore-forming agent within the polymer matrix, among other factors, may also influence pore size and porosity of the polymer matrix.

Where the implant is employed for the purpose of tissue regeneration, as for example, to promote guided tissue regeneration of periodontal tissue, it is preferred that the diameter of the pores in the matrix be effective to deter growth of epithelial cells into the polymer matrix of the implant, and enhance growth of connective tissue cells into the matrix. It is further preferred that the size of the pores and porosity of the matrix of the implant facilitate diffusion of nutrients and other growth-promoting substances such as growth factors, to cells which have grown into the matrix. Preferably, the size of the pores in the polymer matrix is about 3-500 microns, more preferably about 3-200 microns, and most preferably about 75-150 microns.

It is further preferred that the degree of porosity of the matrix provides an implant which is capable of substantially maintaining structural integrity for the desired period of time without breakage or fracturing during use.

Biologically-Active Agent

The composition may further contain at least one biologically-active agent which is capable of providing a biological, physiological or therapeutic effect in an animal. For example it may enhance cell growth and tissue regeneration, act for birth control, cause nerve stimulation or bone growth. The agent may also stimulate other desired biological or physiological activity within the animal. Accordingly, the invention provides an in situ formed implant capable of functioning as a delivery system of drugs, medicaments and other biologically-active agents to tissues adjacent to or distant from the implant site. The biologically-active agent is preferably incorporated into the polymer matrix, and subsequently released into surrounding tissue fluids and to the pertinent body tissue or organ.

Administration of the Composition

The composition may be administered to the implant site by any suitable method for applying a liquid, as for example, by means of a syringe, needle, cannula, catheter, pressure applicator, and the like. In one embodiment, the composition may be administered by means of a syringe directly into integral tissue or into a void or hole such as a periodontal pocket or surgical incision, wherein the mixture in situ forms a solid implant conforming to the shape or the contour of the site. Advantageously, the composition of the invention is useful in overcoming placement difficulties inherent with solid forms of implants.

The invention further provides a method of altering a biological or physiological activity in an animal. The method involves administering to an animal, one of the foregoing compositions in an amount effective to form a solid microporous matrix implant in the animal. The matrix, optionally containing at least one biologically-active agent, is capable of enhancing cell growth and/or tissue formation such as bone or nerve formation, or altering a biological or physiological activity in an animal such as reproductive function and the like.

DETAILED DESCRIPTION OF THE INVENTION

The composition of the invention may be used to provide a biodegradable or bioerodible microporous in situ formed implant in animals. The composition is composed of either a thermoplastic polymer or copolymer in combination with a suitable solvent, or a thermosetting polymer or copolymer containing or combined with a pore-forming means. The polymers or copolymers are substantially insoluble in water and body fluids, biocompatible, and biodegradable and/or bioerodible within the body of an animal. The compositions are administered as a liquid to tissue wherein the implant is formed in situ. The composition is biocompatible and the polymer matrix does not cause substantial tissue irritation or necrosis at the implant site. The implant has a variety of uses, as for example, for enhancing cell growth and tissue regeneration, and delivery of biologically-active agents such as drugs and medicaments.

Thermoplastic Polymer Composition

Thermoplastic polymers useful in the composition of the invention include pharmaceutically compatible polymers that are bioerodible by cellular action, are biodegradable by action of non-living body fluid components, soften when exposed to heat but return to the original state when cooled and are capable of substantially dissolving or dispersing in a water-miscible carrier or solvent to form a solution or dispersion. Upon contact with an aqueous fluid and the dissipation of the solvent component, the thermoplastic polymers are capable of coagulating or solidifying to form a solid or gelatinous matrix suitable for use as an implant in an animal.

The kinds of thermoplastic polymers suitable for the present composition generally include any having the foregoing characteristics. Examples are polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or combinations or mixtures therein. Polylactides, polycaprolactones, polyglycolides and copolymers thereof are highly preferred thermoplastic polymers.

The thermoplastic polymer is combined with a suitable organic solvent to form a solution. The solubility or miscibility of a polymer in a particular solvent will vary according to factors such as crystallinity, hydrophilicity, capacity for hydrogen-bonding and molecular weight of the polymer. Consequently, the molecular weight and the concentration of the polymer in the solvent are adjusted to achieve desired miscibility. Highly preferred thermoplastic polymers are those which have a low degree of crystallization, a low degree of hydrogen-bonding, low solubility in water, and high solubility in organic solvents.

Thermoset Polymer Compositions

The composition of the invention may as well be a liquid formulation of a thermosetting oligomeric pre-polymer or copolymer which is capable of cross-linking or hardening to provide a microporous gelatinous or solid matrix suitable for use as an implant in an animal, including a human. The thermosetting pre-polymers and resulting cross-linked polymers and copolymers are biocompatible, and biodegradable and/or bioerodible.

The pre-polymers are preferably low molecular weight polymers or oligomers having end functional groups that are reactive with acryloyl chloride to produce acrylic ester-terminated pre-polymers. Acrylic pre-polymers for use in the compositions may be synthesized according to a variety of methods including, but not limited to, reaction of a carboxylic acid, such as acrylic or methacrylic acid, with an alcohol; reaction of a carboxylic acid ester, such as methyl acrylate or methyl methacrylate, with an alcohol by transesterification; and reaction of an isocyanatoalkyl acrylate, such as isocyanatoethyl methacrylate, with an alcohol.

The thermosetting prepolymers are also short chain polyol derivatives of the thermoplastic polymers described herein. The polyol terminated derivatives are converted to acrylic ester terminated prepolymers by any suitable method. Examples are short chain polyol derivatives of polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or combinations or mixtures therein.

A preferred polymer matrix and implant prepared with thermosetting prepolymers is composed of poly(DL-lactide-co-caprolactone) (DL-PLC). To prepare the DL-PLC polymer matrix, DL-lactide or L-lactide and $\gamma$-caprolactone are co-polymerized in the presence of a multifunctional polyol initiator and a curing agent to produce hydroxy-terminated PLC prepolymers. This polyol-terminated pre-polymer is then converted to an acrylic ester-terminated pre-polymer by any suitable method, as for example, by acylation of the alcohol terminus with acryloyl chloride by means of, for example, a Schotten-Baumann technique (reaction of acyl halide with alcohol).

Optionally, a curing agent, such as a catalyst, may be added to the acrylic pre-polymer mixture to enhance cross-linking of the pre-polymers and the subsequent coagulation or solidification of the resulting polymer to form a matrix. For example, the acrylic pre-polymer, in an amount of about 5 grams, may be added to a solution of benzoyl peroxide (BP) in about 1 ml of $CH_2Cl_2$. Optionally, other acrylic monomers may be added to the acrylic pre-polymer mixture before adding the curing agent. The acrylic pre-polymer mixture may be cured in air at room temperature, or in a preheated vacuum oven.

Preferred catalysts for the preparation of the PLC prepolymers are basic or neutral ester-interchange (transesterification) catalysts, as for example, metallic esters of carboxylic acids containing up to 18 carbon atoms, formic, acetic, lauric, stearic, and benzoic acid. Preferred catalysts include, for example, stannous octoate and stannous chloride.

A multi-functional polyol chain initiator may be included in the thermosetting polymer compositions to vary the molecular weight and composition of the polymer. For example, a bifunctional chain initiator such as ethylene glycol, may be included to produce a bifunctional polymer, or a trifunctional initiator, such as trimethylolpropane, may be used to produce a trifunctional polymer. Further, the molecular weight of the polymer or co-polymer may be varied according to the concentration of the chain initiator in the composition. For example, a high concentration of a bifunctional chain initiator may make available an initiator molecule for each polymer chain, while a low concentration may contain one initiator molecule for every two polymer chains.

Following the addition of the curing agent, the pre-polymer polymer mixture preferably remains in liquid form for a period of time effective to allow administration of the composition to the implant site. Thereafter, the cross-linking reaction preferably continues until a solid or gelatinous polymer matrix is produced. Accordingly, the pre-polymer mixture cures, or solidifies, in situ to form a polymer matrix which is capable of biodegradation and/or bioabsorption over time.

The thermoset polymer composition contains one or more materials to form the microporous matrix. The polymer itself can contain moieties that are released as volatile substances during cross-linking to cause pore-formation. Alternatively, the composition can contain a minimum amount of suitable, biocompatible organic solvent as described below, or can contain a separate pore-forming agent as discussed below. The thermoset polymers containing releaseable moieties are known in the art.

Solvents

Solvents suitable for the thermoplastic polymer composition are those which are biocompatible, preferably pharmaceutically acceptable, miscible with the polymer component and water, and capable of diffusing into tissue fluids surrounding the implant site. Preferably, the solvent has a Hildebrand (HLB) solubility ratio of from about $9(cal/cm^3)^{\frac{1}{2}}$ to $13(cal/cm^3)^{\frac{1}{2}}$. The degree of polarity of the solvent should be effective to provide at least about 10% solubility in water, and to dissolve or disperse the polymer component into solution.

According to the invention, the composition is administered to the implant site in liquid form, whereupon the solvent diffuses into the adjacent tissue fluids. Upon contact with the surrounding aqueous fluids, the polymer moiety coagulates or solidifies to form a solid or gelatinous matrix fitting the usually irregular shape of the incision or void of the implant site. Preferably, the solvent quickly diffuses into the surrounding tissue fluids to enhance formation of the polymer matrix following administration of the composition to the implant site. Preferably, the polymer matrix is capable of adhering to the adjacent tissue by mechanical forces to at least partially bond or attach the implant to the adjacent tissue, and/or mechanically bond two tissues together. The concentration of polymer in solvent for the composition will generally accomplish rapid and effective dissipation of the solvent and coagulation of the polymer. This concentration may range from 0.01 g of polymer per ml of solvent to a saturated concentration, preferably from 0.1 g per ml to saturation.

Solvents which may be used in the thermoplastic polymer composition of the invention include, for example, N-methyl-2-pyrrolidone, 2-pyrrolidone, $C_2$ to $C_6$ alkanols, propylene glycol, acetone, alkyl esters such as methyl acetate, ethyl acetate, ethyl lactate, alkyl ketones such as methyl ethyl ketone, dialkylamides such as dimethylformamide, dimethyl sulfoxide, dimethyl sulfone, tetrahydrofuran, cyclic alkyl amides such as caprolactam, decylmethylsulfoxide, oleic acid, propylene carbonate, aromatic amides such as N,N-diethyl-m-toluamide, and 1-dodecylazacycloheptan-2-one. Preferred solvents according to the invention include N-methyl-2-pyrrolidone, 2-pyrrolidone, dimethyl sulfoxide, acetone, and propylene carbonate.

A mixture of solvents may be used to increase the coagulation rate of polymers which exhibit a slow coagulation or setting rate. For example, the polymer may be combined with a coagulant-promoting solvent system composed of a mixture of a good solvent and a poorer solvent or a non-solvent for the polymer component. It is preferred that the solvent mixture contain an effective amount of the two solvents such that the polymer will remain soluble in the mixture but coagulate upon dissipation or diffusion of the solvents into surrounding tissue fluids at the implant site.

The same solvents can also be combined with the thermoset polymer composition. In this variation, the solvent does not form the liquid character of the composition. The prepolymer itself is liquid. Instead the solvent acts to produce the two component porous matrix discussed below. The solvent concentration is at a minimum for such purpose and is preferably inert toward the cross-linking reaction. The solvent diffuses as the prepolymer hardens to form the solid implant matrix. The organic solvent is included in the thermosetting polymer composition in an amount suitable to form pores but not high enough to substantially dilute the pre-polymer ingredient to a condition where it only lightly cross-links.

Pore-Formation and Porosity

Upon contact with an aqueous body fluid or water, the thermoplastic polymer composition coagulates or solidifies to form a microporous gelatinous or solid matrix. Similarly, the thermoset polymer composition hardens to form a microporous solid matrix. In either variation, pores may be formed within the matrix by several means. Dissipation, dispersement or diffusion of the solvent or released moiety (thermoset polymer) out of the solidifying polymer matrix or hardening polymer matrix (thermoset polymer) and into the adjacent tissue fluids may generate pores, including pore channels, in the polymer matrix.

Diffusion of the solvent or released moiety produces a thermoplastic or thermoset polymer matrix having a two component structure, that is, an inner core portion or layer, and an outer surface portion or skin. The pores of the core are substantially uniform while by comparison with the porous nature of the core, the skin is essentially non-porous. In fact, the skin has pores with diameters significantly smaller in size than those in the core.

Pore-Forming Agent

In either the thermoplastic or thermoset polymer composition, a pore-forming agent may be included to generate additional pores in the polymer matrix. The pore-forming agent is biocompatible, and soluble in body fluids and water as well as in the organic solvents. The pore-forming agent is further capable of diffusing or dispersing out of the coagulating polymer matrix and into the adjacent fluids, whereupon pores are generated in the polymer matrix.

The pore-forming agent, when combined with the thermoplastic polymer and solvent or with the thermoset polymer optionally containing a minimal amount of solvent, preferably forms a uniform mixture with the polymer either as a dispersion or suspension, or as a solution. When the mixture is administered to an implant site, the solvent and/or pore-forming agent preferably dissipate or diffuse into surrounding tissue fluids causing the formation of microporous channels within the coagulating polymer matrix. Optionally, the pore-forming agent may become incorporated into the polymer matrix, and dissipate into the surrounding tissue fluids at a rate slower than that of the solvent, or be released from the matrix by biodegradation or bioerosion. The porous matrices formed through the inclusion of a pore-forming agent have a pore structure in which the pores are substantially similar in size throughout the matrix structure.

Preferably, the pore-forming agent is combined with the thermoplastic polymer and solvent, or the thermoset pre-polymer or copolymer mixture before the matrix is formed. The pore-forming agent may form a mixture solution or dispersion with the polymer.

Pore-forming agents include, any pharmaceutically acceptable organic or inorganic water-soluble substance that is substantially miscible in water and body fluids and will dissipate from the in situ formed matrix into body fluids. The pore-forming agent may also be a water-immiscible substance that rapidly degrades to a water-soluble substance. In the thermoplastic polymer composition of the invention, it is further preferred that the pore-forming agent is miscible or dispersible in the organic solvent to form a uniform mixture with the polymer moiety. Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and polyvinylpyrrolidone.

The concentration of pore-forming agent relative to polymer in the composition will vary according to the degree of pore-formation desired. Generally, this concentration will range from 0.01 g of pore-forming agent per gram of polymer to about 1 g per gram.

The size or diameter of the pores formed in the matrix may be modified by the size and/or distribution of the pore-forming agent within the polymer matrix. For example, pore-forming agents which are relatively insoluble in the polymer mixture, may be selectively included in the composition according to particle size to generate pores having a diameter which corresponds to the size of the pore-forming agent. Pore-forming agents which are soluble in the polymer mixture may vary the pore size and porosity of the polymer matrix according to the pattern of distribution and/or aggregation within the mixture and resulting polymer matrix.

The concentration of water-soluble components, such as the solvent and/or pore-forming agent, in the composition may vary the porosity of the polymer matrix. For example, a composition having a high concentration of water-soluble substances may produce a polymer matrix having a high degree of porosity.

To provide an effective implant for bone cell regrowth and tissue regeneration, it is preferred that the diameter of the pores be about 3–500 microns, more preferably about 3–200 microns, and most preferably 75–150 microns. It is further preferred that the matrix has a porosity of about 5–95%, preferably about 25–85% in order to provide optimum cell and tissue ingrowth into the matrix and optimum structural integrity.

Pore diameter and distribution within the polymer matrix may be measured, as for example, according to scanning electron microscopy methods by examination of cross-sections of the polymer matrix. Porosity of the polymer matrix may be measured according to any suitable method, as for example, mercury intrusion porosimetry, specific gravity or density comparisons, calculation from scanning electronic microscopy photographs, and the like. Additionally, porosity may be calculated according to the proportion or percent of water-soluble material included in the polymer composition. For example, a composition which contains about 30% polymer and about 70% solvent and/or other water-soluble components will generate a polymer matrix having about 70% porosity.

Preferably, the pore-forming agent is dissipated immediately from the polymer matrix to generate a matrix having a porosity and pore structure effective to perform the particular purpose of the implant, as for example, a tissue regeneration site or a matrix for timed-release of a drug or medicament.

Implant For Tissue Regeneration

The composition may be administered to an implant site, as for example, whole tissue or tissue with a void such as a periodontal pocket, a soft-tissue defect, a surgical incision, and the like. When the composition is administered to a tissue regeneration site, it is preferred that the implant provides a surface to facilitate the growth of regenerative tissue. For example, to enhance regeneration of hard tissue such as bone tissue, it is preferred that the polymer matrix will provide a support for new bone cell growth which will replace the matrix as it is gradually absorbed or eroded by body fluids.

The microporous polymer matrix is capable of biodegradation and/or bioabsorption within the implant site. According to the invention, the particular polymer and the molecular weight of the polymer may vary in the composition according to a desired duration or time interval of the degradation or bioerosion of the polymer matrix, as for example, a few weeks or several years. When the implant is used to enhance cell growth and tissue regeneration, it is preferred that the matrix disintegrate at a rate effective to allow replacement of the matrix by cell growth from the adjacent cells or tissue.

Biologically-Active Agent

The in situ formed implants may also provide a delivery system for biologically-active agents to adjacent or distant body tissues and organs. Biologically-active agents which may be used alone or in combination in the present compositions and implants include medicaments, drugs, or any suitable biologically-, physiologically- or pharmacologically-active substance which is capable of providing local or systemic biological or physiological activity in an animal, including a human, and which is capable of being released from the polymer matrix into an adjacent or surrounding aqueous fluid.

The biologically-active agent may be miscible in the polymer and/or solvent to provide a homogenous mixture with the polymer, or insoluble in the polymer and/or solvent to form a suspension or dispersion with the polymer. It is highly preferred that the biologically-active agent be combined with the thermosetting polymer composition almost immediately prior to administration of the composition to the implant site. It is further preferred that the bioactive agent will not contain functional groups which will interfere with the cross-linking reaction of the thermoset polymer. These conditions are readily determined by those of skill in the art simply by comparing the structure of the bioactive agent and the reacting moieties of the thermoset polymer.

Upon administration of the composition to the implant site, the biologically-active agent preferably becomes incorporated into the polymer matrix. As the matrix biodegrades and/or bioerodes, the biologically-active agent may be released from the matrix into the adjacent tissue fluids. Preferably, the biologically-active agent is released into the surrounding tissue fluids at a controlled rate. For example, the polymer matrix may be formulated to degrade after an effective and/or substantial amount of the biologically-active agent is released from the matrix. Release of a biologically-active agent having a low solubility in water, as for example a peptide or protein, may require the degradation of a substantial part of the polymer matrix to expose the agent directly to the surrounding tissue fluids. Thus, the release of the biologically-active agent from the matrix may be varied by, for example, the solubility of the biologically-active agent in water, the distribution of the biologically-active agent within the matrix, or the size, shape, porosity, solubility and biodegradability of the polymer matrix, among other factors.

The composition and in situ formed implant contain the biologically-active agent in an amount effective to provide a desired biological, physiological, pharmacological and/or therapeutic effect, optionally according to a desired release profile, and/or time duration of release. It is further preferred that the biologically-active agent is included in the polymer composition in an amount effective to provide an acceptable solution or dispersion viscosity.

In addition, the biologically-active agent may act as a pore-forming agent, or substance capable of generating pores in the polymer matrix of the implant. To enhance selective cell growth into the matrix, for example, it is preferred that the bioactive agent is released from the polymer matrix at a rate corresponding to that of cell migration and growth into newly formed pores of the matrix.

The biologically-active agent may also be a substance, or metabolic precursor thereof, which is capable of promoting growth and survival of cells and tissues, or augmenting the activity of functioning cells, as for example, blood cells, neurons, muscle, bone marrow, bone cells and tissues, and the like. For example, the biologically-active agent may be a nerve growth promoting substance, as for example, a ganglioside, phosphatidylserine, a nerve growth factor, brain-derived neurotrophic factor, a fibroblast growth factor, and the like. In particular, the in situ implants are capable of enhancing regeneration of the periodontium by providing an outer surface having a porosity which serves as a physical barrier between an exposed root surface and encroaching epithelial cells to promote guided tissue regeneration.

To promote tissue growth, the biologically-active agent may be either a hard or soft tissue promoting substance or combinations thereof. Suitable tissue growth promoting agents include, for example, fibronectin (FN), endothelial cell growth factor (ECGF), cementum attachment extracts (CAE), human growth hormone (HGH), a Periodontal ligament cell growth factor, fibroblast growth factor (FGF), animal growth hormones, platelet derived growth factor (PDGF), epidermal growth factor (EGF), protein growth factor interleukin-1 (IL-1), transforming growth factor (TGFβ-2), insulin-like growth factor II (ILGF-II), human alpha thrombin (HAT), osteoinductive factor (OIF), bone morphogenetic protein (BMP) or protein derived therefrom, demineralized bone matrix, and releasing factors thereof.

Further, the agent may be a bone growth promoting substance such as hydroxyapatite, tricalcium phosphate, a di- or polyphosphonic acid, an anti-estrogen, a sodium fluoride preparation, a substance having a phosphate to calcium ratio similar to natural bone, and the like. A bone growth promoting substance may be in the form, as for example, of bone chips, bone crystals or mineral fractions of bone and/or teeth, a synthetic hydroxyapatite, or other suitable form. The agent may further be capable of treating metabolic bone disorders such as abnormal calcium and phosphate metabolism by, for example, inhibiting bone resorption, promoting bone mineralization, or inhibiting calcification.

See, for example, U.S. Pat. No. 4,939,131 to Benedict et al., U.S. Pat. No. 4,942,157 to Gall et al., U.S. Pat. No. 4,894,373 to Young, U.S. Pat. No. 4,904,478 to Walsdorf et al., and U.S. Pat. No. 4,911,931 to Baylink, U.S. Pat. No. 4,916,241 to Hayward et al., U.S. Pat. No. 4,921,697 to Peterlik et al., U.S. Pat. No. 4,902,296 to Bolander et al., U.S. Pat. No. 4,294,753 to Urist, U.S. Pat. No. 4,455,256 to Urist, U.S. Pat. No. 4,526,909 to Urist, U.S. Pat. No. 4,563,489 to Urist, U.S. Pat. No. 4,596,574 to Urist, U.S. Pat. No. 4,619,989 to Urist, U.S. Pat. No. 4,761,471 to Urist, U.S. Pat. No. 4,789,732 to Urist, U.S. Pat. No. 4,795,804 to Urist, and U.S. Pat. No. 4,857,456 to Urist, the disclosures of which are incorporated by reference herein.

Suitable biologically-active agents also include substances useful in preventing infection at the implant site, as for example, antiviral, antibacterial, antiparasitic, antifungal substances and combinations thereof. The agent may further be a substance capable of acting as a stimulant, sedative, hypnotic, analgesic, anticonvulsant, and the like.

The delivery system can contain a large number of biologically-active agents either singly or in combination. Examples of these biologically-active agents include, but are not limited to:

Anti-inflammatory agents such as hydrocortisone, prednisone, fludrotisone, triamcinolone, dexamethasone, betamethasone and the like.

Anti-bacterial agents such as penicillins, cephalosporins, vancomycin, bacitracin, polymycins, tetracyclines, chloramphenicol, erythromycin, streptomycin, and the like.

Antiparasitic agents such as quinacrine, chloroquine, quinine, and the like.

Antifungal agents such as nystatin, gentamicin, miconazole, tolnaftate, undecyclic acid and its salts, and the like.

Antiviral agents such as vidarabine, acyclovir, ribarivin, amantadine hydrochloride, iododeoxyuridine, dideoxyuridine, interferons and the like.

Antineoplastic agents such as methotrexate, 5-fluorouracil, bleomycin, tumor necrosis factor, tumor specific antibodies conjugated to toxins, and the like.

Analgesic agents such as salicylic acid, salicylate esters and salts, acetaminophen, ibuprofen, morphine, phenylbutazone, indomethacin, sulindac, tolmetin, zomepirac, and the like.

Local anaesthetics such as cocaine, benzocaine, novocaine, lidocaine, and the like.

Vaccines such as hepatitis, influenza, measles, mumps, rubella, hemophilus, diphtheria, tetanus, rabies, polio, and the like.

Central nervous system agents such as tranquilizers, sedatives, anti-depressants, hypnotics, B-adrenergic blocking agents, dopamine, and the like.

Growth factors such as colony stimulating factor, epidermal growth factor, erythropoietin, fibroblast growth factor, neural growth factor, human growth hormone, platelet derived growth factor, insulin-like growth factor, and the like.

Hormones such as progesterone, estrogen, testosterone, follicle stimulating hormone, chorionic gonadotrophin, insulin, endorphins, somatotropins and the like.

Antihistamines such as diphenhydramine, chlorpheneramine, chlorcyclizine, promethazine, cimetidine, terfenadine, and the like.

Cardiovascular agents such as verapamil hydrochloride, digitalis, streptokinase, nitroglycerine paparefine, disopyramide phosphate, isosorbide dinitrate, and the like.

Anti-ulcer agents such as cimetidine hydrochloride, isopropamide iodide, propantheline bromide, and the like.

Bronchodilators such as metaproternal sulfate, aminophylline, albuterol, and the like.

Vasodilators such as theophylline, niacin, nicotinate esters, amylnitrate, minoxidil, diazoxide, nifedipine, and the like.

The biologically-active agent may be included in the compositions in the form of, for example, an uncharged molecule, a molecular complex, a salt, an ether, an ester, an amide, or other form to provide the effective biological or physiological activity.

Administration of the composition of the invention ultimately will be accomplished according to the wisdom and protocol of the patient's attending health care professional such as a physician, or if appropriate, a dentist. Choice of the particular composition will depend upon the malcondition or condition to be treated, which choice will be made by the attending health care professional. Application by syringe, or other means for applying a liquid to or into a tissue may be employed. Without a bioactive agent, the composition can function as a structure for promotion of cell growth and tissue repair. With a bioactive agent, the composition will not only function in such capacity but will also adopt the properties of the bioactive agent.

The amounts and concentrations of composition administered to the patient will generally be sufficient to accomplish the task intended. If that task is void space filling, enough composition will be administered to accomplish this task. For administration of bioactive agent, the amounts and release rates will follow recommendations of the manufacturer of the bioactive agent. Generally, the concentration of bioactive agent in the liquid polymer mixture will be from 0.01 mg per g of mixture to 400 mg per g of mixture.

Advantageously, the polymer compositions may be administered to an implant site, as for example, by injection with a syringe, whereupon the composition will solidify in situ. The resulting implant may thus be administered to an implant site without the need for surgical incision.

The invention will be described with reference to various specific and preferred embodiments and techniques. However, it should be understood that many variations and modifications may be made while remaining within the spirit and scope of the invention.

EXAMPLE 1

A mixture comprising about 5% equimolar mixture of sodium carbonate and citric acid, about 34.8% poly(DL-lactide) (DL-PLA) and about 60.2% N-methyl pyrrolidone (NMP) was prepared by suspending sodium carbonate and citric acid in the polymer solution. The DL-PLA polymer had a molecular weight of about 30,000 daltons (inherent viscosity of 0.38 dL/g).

One drop of the mixture was precipitated into a vial containing phosphate-buffered saline (PBS) or water. The vial was placed in a 37° C. shaker bath for about 48 hours. The sample was then removed from the bath, and dried in vacuo prior to examination by Scanning Electron Microscopy (SEM). The resulting article was porous with pores of about $5\mu$ in diameter, and a porosity of about 65%.

EXAMPLE 2

A mixture comprising about 5% sucrose, about 34.8% DL-PLA and about 60.2% NMP was prepared according to Example 1. A porous article was produced having pores of about $3\mu$ in diameter and a porosity of about 65%.

EXAMPLE 3

A mixture comprising about 5% poly(vinyl pyrrolidone)(PVP), about 34.8% DL-PLA and about 60.2% NMP was prepared according to Example 1. A porous article was produced having pores of about $5-10\mu$ in diameter and a porosity of about 65%.

EXAMPLE 4

A mixture comprising about 10% PVP, about 33.0% DL-PLA, and about 57.0% NMP was prepared according to Example 1. A porous article was produced having pores of about $5-20\mu$ in diameter and a porosity of about 65%.

EXAMPLE 5

In this example, a mixture was prepared comprising about 50% of two different molecular weights of DL-PLA and about 50% NMP. A water-soluble, low molecular weight DL-PLA (molecular weight of about 2000 daltons) was mixed with a higher molecular weight DL-PLA with an inherent viscosity of 0.38 dL/g (molecular weight of about 30,000 daltons). The DL-PLA mixture was dissolved in NMP to provide a mixture comprised of about 38% low molecular weight DL-PLA, about 12% higher molecular weight DL-PLA, and about 50% NMP. This mixture was then precipitated, incubated and dried according to Example 1. A porous article was producing having pores of about $10-50\mu$ in diameter, and about 50% porosity.

EXAMPLE 6

A mixture comprising about 5% ethoxydihydrosanguinarine (SaOEt), 27.5% DL-PLA and 67.5% NMP was prepared according to Example 1. SaOEt is an antimicrobial agent derivable from benzophenanthridine alkaloids. A porous article was produced having pores of about $15-30\mu$ in diameter and about 70% porosity.

EXAMPLE 7

A mixture comprising about 5% SaOEt, 27.5% DL-PLA and 67.5% NMP was prepared according to Example 1, the DL-PLA component having a molecular weight of about 10,000 daltons. A porous article was produced having pores of about $4-8\mu$ in diameter. A wet sample of the article was examined by X-ray tomography by scanning at intervals of about 0-25 mm. The articles showed porosity throughout with about 70% porosity.

EXAMPLE 8

An implant comprising about 5.0% sanguinarine chloride (SACl), about 47.5% DL-PLA, and about 47.5% NMP was administered to a periodontal pocket of a human patient. SaCl is an antimicrobial and anti-inflammatory agent derivable from benzophenanthridine alkaloids. After 28 days, the implant was removed, dried in vacuo and examined by SEM. Pores having a diameter of about $1-2\mu$ and of about $10-20\mu$ were detected. Approximately 50% of the pores were $10-20\mu$. The implant had a total porosity of about 50%.

EXAMPLE 9

A mixture comprising about 33% PVP, about 33% 50/50 copolymer of DL-lactide and glycolide (DL-PLG), and about 34% NMP was prepared according to Example 1. A porous article was produced having pores of about $3-10\mu$. Examination of the article showed that the pores were arranged in an interconnecting network. The article had a porosity of about 65%.

EXAMPLE 10

A lyophilized sample of fibronectin, a tissue growth and cell attachment factor, was added to a solution of DL-PLA in NMP to provide a dispersion comprising about 13.2% wt-% lyophilized fibronectin, about 30.4 wt-% DL-PLA, and about 56.4 wt-% NMP. As a result of the lyophilization process, the lyophilized fibronectin contained various salts with only about 0.89% active component. This dispersion was added to a phosphate-buffered receiving solution wherein it coagulated into a solid matrix. The receiving solution was maintained at 37° C. under agitation and changed periodically to preclude a high concentration of fibronectin within the receiving solution. The receiving solution was analyzed for total protein concentration by the Pierce BCA protein assay. The cumulative percentage of fibronectin released from the matrix was calculated. About 12% of the fibronectin component was released after one day, about 25% after 2 days, about 26% after 3 days, about 28% after 4 days, 30% after 5 days, and 33% after 7 days. The porosity of the solid matrix of the implant was initially about 55%. The porosity level of the matrix increased as the fibronectin component was released over time. The pores of greater than $3\mu$ in diameter were produced by the dissolving fibronectin component.

EXAMPLE 11

Norethindrone and ethinylestradiol, birth control agents, may be added to a solution of DL-PLA in NMP to provide a liquid mixture containing about 10% wt. % norethindrone, about 1 wt. % ethinylestradiol, about 33 wt. % DL-PLA and about 56 wt. % NMP. The mixture can then be injected under the skin of an animal where it coagulates to form a solid microporous implant. Levels of norethindrone and ethinylestradiol in the blood can be measured over time. The effect on rates of pregnancy can also be measured. The implant advantageously functions to release birth control agents continuously over time and does not have to be removed by surgery.

EXAMPLE 12

Terfenadine, an antiallergy medication, may be added to a solution of DL-PLA in NMP to provide a liquid mixture containing about 10 wt. % terfenadine, about 33 wt. % DL-PLA and 57 wt. % NMP. The mixture can then be injected under the skin of an animal where it coagulates to form a solid microporous implant. The level of terfenadine in the blood can be measured over time. The efficacy of the implant in controlling allergy symptoms can also be measured.

EXAMPLE 13

Bone chips and bone morphogenetic protein can be added to form a liquid mixture containing about 10 wt. % bone chips, about 1 wt. % bone morphogenetic protein, about 5 wt. % PVP, about 33 wt. % DL-PLA, and about 51 wt. % NMP. The mixture can then be injected to fill in a bone defect in a crushed cheekbone. The mixture coagulates in situ, conforming to the shape of the site, and filling in the damaged tissue. Healing and regeneration of bone tissue can be monitored over time.

EXAMPLE 14

Ovine follicle stimulating hormone, an ovulation stimulatory agent, may be added to form a liquid mixture containing about 2 wt. % ovine follicle stimulating hormone, about 41 wt. % DL-PLA, and about 57 wt. % NMP. The solution can be injected subdermally into a cow to form a solid microporous implant. The ovulation rate can be measured 4–6 days after oestrus.

What is claimed is:

1. A composition suitable for forming an in situ solid implant in an animal, comprising: a liquid formulation of a biodegradable, bioerodible, biocompatible thermoplastic polymer that is insoluble in aqueous or body fluid, and a biocompatible organic solvent that is miscible or dispersible in aqueous or body fluid and dissolves the thermoplastic polymer, the composition being capable of coagulating or solidifying to form a solid or gelatinous microporous matrix upon its contact with aqueous or body fluid, the matrix being a core surrounded by a skin, the core containing pores of diameters from about 1 to about 1000 microns, and the skin containing pores of smaller diameters than those of the core pores.

2. A composition according to claim 1, wherein the skin pores are of a size such that the skin is functionally non-porous in comparison with the core.

3. A method of forming an implant suitable for providing a biological, therapeutic or physiological effect in an animal, comprising: administering to the animal a composition in an amount effective to form in situ a solid implant, the composition being a liquid formulation of a biodegradable, bioerodible, biocompatible thermoplastic polymer that is insoluble in aqueous or body fluid, and a biocompatible organic solvent that is miscible or dispersible in aqueous or body fluid and dissolves the thermoplastic polymer, and the composition undergoing coagulation or solidification of the polymer and dispersion of the solvent into body fluid to form a solid or gelatinous microporous matrix, the matrix being a core surrounded by a skin, the core containing pores of diameters from about 1 to 1000 microns and the skin containing pores of small diameters than those of the core pores.

4. A composition suitable for forming an in situ solid implant in an animal, comprising: a liquid formulation of a biodegradable, bioerodable, biocompatible thermoplastic polymer that is insoluble in aqueous or body fluid, a biocompatible organic solvent that is miscible or dispersible in aqueous or body fluid and dissolves the thermoplastic polymer, and a pore-forming agent, the composition being capable of coagulating or solidifying to form a solid or gelatinous microporous matrix upon its contact with an aqueous or body fluid, the matrix being a core surrounded by a skin, and the skin and core containing pores within the same range of diameters, that range being from about 1 to about 1000 microns.

5. A composition according to claim 4, wherein the pore-forming agent is a sugar, salt, or water-soluble polymer, or water-insoluble substance that degrades to a water soluble substance.

6. A composition according to claim 1, wherein the thermoplastic polymer is selected from the group consisting of polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, polymalic acid, polyamino acids, polymethyl vinyl ether, chitin, chitosan, and copolymers, terpolymers, and any combination thereof.

7. A composition according to claim 1, wherein the solvent is selected from the group consisting of N-methyl-2-pyrrolidone, 2-pyrrolidone, ethanol, propylene glycol, propylene carbonate, acetone, acetic acid, ethyl acetate, ethyl lactate, methyl acetate, methyl ethyl ketone, dimethylformamide, dimethyl sulfoxide, dimethyl sulfone, tetrahydrofuran, caprolactam, decylmethylsulfoxide, oleic acid, N,N-diethyl-m-toluamide, and 1- dodecylazacycloheptan-2-one, and any combination thereof.

8. A composition according to claim 1, further comprising at least one biologically-active agent.

9. A composition according to claim 8, wherein the biologically-active agent is a polypeptide derived from a natural, synthetic, or recombinant DNA source.

10. A composition according to claim 8, wherein the biologically-active agent is selected from a group consisting of anti-inflammatory agents, antibacterial agents, antiparasitic agents, antifungal agents, antiviral agents, anti-neoplastic agents, analgesic agents, anaesthetics, vaccines, central nervous system agents, growth factors, hormones, antihistamines, osteoinductive agents, cardiovascular agents, anti-ulcer agents, bronchodilators, vasodilators, birth control agents, and fertility enhancing agents.

11. A composition suitable for forming an in situ solid implant in an animal, comprising: a liquid formulation of a biodegradable, bioerodable, biocompatible thermoset polymer that is insoluble in aqueous or body fluid, and an agent selected from the group consisting of a pore-forming agent, a biocompatible organic solvent that is miscible or dispersible in aqueous or body fluid and a releasible, pore-forming moiety within the thermoset polymer; the composition being capable of forming a solid microporous matrix, the matrix being a core surrounded by a skin and the core containing pores of diameters from about 1 to about 1000 microns.

12. A composition according to claim 11, wherein the skin contains pores of smaller diameters than those of the core pores such that the skin is functionally non-porous in comparison with the core.

13. A composition according to claim 11, wherein the core and skin contain pores within the same range of diameters.

14. A method of forming an implant suitable for providing a biological, therapeutic or physiological effect in an animal, comprising: administering to the animal a composition in an amount effective to form in situ a solid implant, the composition being a liquid formulation of a biodegradable, bioerodable, biocompatible thermoset polymer that is insoluble in aqueous or body fluid, and an agent selected from the group consisting of a pore-forming agent, a biocompatible organic solvent that is miscible or dispersible in aqueous or body fluid and a releasible, pore-forming moiety within the thermoset polymer; and the composition undergoing curing to form a microporous matrix, the matrix being a core surrounded by a skin and the core containing pores of diameters from about 1 to 1000 microns.

15. A composition according to claim 11 wherein the pore-forming agent is a sugar, salt, water-soluble polymer, or water-miscible organic solvent.

16. A composition according to claim 11, wherein the polymer is an acrylic ester-terminated biodegradable prepolymer capable of cross-linking to form a polymer matrix.

17. A composition according to claim 16, wherein the acrylic ester-terminated biodegradable prepolymer is selected from the group consisting essentially of polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, polymalic acid, polyamino acids, polymethyl vinyl ether, chitin, chitosan, and copolymers, terpolymers, and any combination thereof.

18. A composition according to claim 11, further comprising a curing agent.

19. A composition according to claim 11, further comprising at least one biologically-active agent that is free of functional groups that would interfere with the thermosetting reaction of the thermoset polymer.

20. A composition according to claim 19, wherein the biologically-active agent is a polypeptide derived from a natural, synthetic, or recombinant DNA source.

21. A composition according to claim 19, wherein the biologically-active agent is selected from a group consisting of anti-inflammatory agents, antibacterial agents, antiparasitic agents, antifungal agents, antiviral agents, anti-neoplastic agents, analgesic agents, anaesthetics, vaccines, central nervous system agents, growth factors, hormones, antihistamines, osteoinductive agents, cardiovascular agents, anti-ulcer agents, bronchodilators, vasodilators, birth control agents and fertility enhancing agents.

22. A method according to claim 3, wherein the implant is capable of enhancing tissue regeneration.

23. A method according to claim 3, wherein the implant is capable of filling in defects in tissue.

24. A method according to claim 3, wherein the composition further comprises at least one biologically-active agent.

25. A method according to claim 24, wherein the biologically active agent is selected from the group consisting of anti-inflammatory agents, antibacterial agents, antiparasitic agents, antifungal agents, antiviral agents, anti-neoplastic agents, analgesic agents, anaesthetics, vaccines, central nervous system agents, growth factors, hormones, antihistamines, osteoinductive agents, cardiovascular agents, anti-ulcer agents, vasodilators, bronchodilators, birth control agents, and fertility enhancing agents.

26. A method of claim 24, wherein the biologically-active agent has a biological or physiological therapeutic effect of the reproductive system.

* * * * *

UNITED STATES PATENT AND TRADEMARK OFFICE
CERTIFICATE OF CORRECTION

PATENT NO. : 5,324,519
DATED : June 28, 1994
INVENTOR(S) : Dunn et al.

It is certified that error appears in the above-indentified patent and that said Letters Patent is hereby corrected as shown below:

At col. 12, line 51, for "paparefine" read --papaverine--.

In claim 3 at col. 16, line 31, for "small" read --smaller--.

Signed and Sealed this

Sixth Day of June, 1995

*Attest:*

BRUCE LEHMAN

*Attesting Officer*  *Commissioner of Patents and Trademarks*